United States Patent [19]

Barberet et al.

[11] Patent Number: Plant 7,184

[45] Date of Patent: Mar. 6, 1990

[54] CARNATION NAMED LONRAILOR

[75] Inventors: Nicole Barberet; Henri Blanc, both of Antibes, France; Antonio Di Giorgio; Renato Di Giorgio, both of San Remo, Italy

[73] Assignee: Etablissements Barberet et Blanc, La Londe-les-Maures, France

[21] Appl. No.: 315,021

[22] Filed: Feb. 24, 1989

[51] Int. Cl.[4] ..... A01H 5/00

[52] U.S. Cl. ..... Plt./73

[58] Field of Search ..... Plt./73

*Primary Examiner*—James R. Feyrer

*Attorney, Agent, or Firm*—Charles W. Rummler

[57] ABSTRACT

A new carnation cultivar as characterized by its brilliant dark ruby red color of its medium sized blooms which are profusely produced, borne singly on sturdy, long stems and having a recurrent blooming habit.

1 Drawing Sheet

BACKGROUND OF THE NEW PLANT

The new carnation cultivar originated at San Remo, Italy as a seedling of a hybrid developed in 1985 at the nursery maintained by Antonio and Renato Di Giorgio by crossing two varieties selected from their collection of carnations maintained at their nursery for breeding purposes. This particular seedling was selected for propagation because of its profuse production of brilliant dark ruby red medium sized flowers borne on strong, upright stems of a plant having a height of about 130 cm. at eight months growth. Propagation of this plant through successive generations by means of cuttings and in vitro propagation at San Remo has demonstrated that the new plant has not only retained the continuous and abundant production capability required for commercial purposes, but also that its distinguishing characteristics hold true from generation to generation and appear to be firmly fixed.

Accordingly, our new carnation variety is now being propagated for commercial purposes by means of cuttings, as well as by in vitro propagation procedures, at Establissements Barberet et Blanc, Laboratoire de Physiologie Vegetale, 83250 La Londe-Les Maures, France.

DESCRIPTION OF THE DRAWING

Our new carnation variety is illustrated by the accompanying photographic drawing, which shows several blooming stems with flowers and buds in several stages of development, the color rendition being as nearly true to that herein specified as is reasonably possible to obtain by professional photographic procedures.

DESCRIPTION OF THE NEW PLANT

The following is a detailed description of our new carnation variety based upon observations made in the Spring of 1988 of plants grown in greenhouse, as well as outside, at San Remo, Italy, the color designations stated herein being according to The R.H.S. Colour Chart published by The Royal Horticultural Society of London, England.

THE PLANT

Origin: Seedling.

Parentage:

*Seed parent.*—Variety No. 845.

*Pollen parent.*—Variety No. 291.

Both parents are unpatented and unnamed and are identified in the breeding records maintained in the Di Giorgio nursery office at Via Villetta 41, 18038 San Remo, Italy.

Classification:

*Botanic.*—*Dianthus caryophyllus.*

*Commercial.*—Standard Carnation.

Form: A tall, erect bush having at least four stems emitted near the ground.

Height: Averages about 130 cm. at eight months of growth.

Main stem length: Less than 15 cm. due to pinching.

Branching: This plant is branched.

Growth: Vigorous and upright.

Foliage:

*Quantity.*—Moderately abundant.

*Number of leaves.*—More than 120.

*Leaf size.*—(At the seventh node) About 13.9 cm. long and 0.83 cm. wide.

*Leaf shape.*—Oblong — With curved margins.

*Texture.*—Leathery.

*Color.*—Both upper and under sides, 189-A/B.

THE BUD

Size: Large.

*Diameter.*—Averages about 2.4 cm.

*Length.*—Averages about 3.3 cm.

Shape:

*Spherical.*—Globular.

Rate of opening: Normal.

Color of petals: When sepals first divide and petals begin to unfurl: the same as at full bloom.

Sepals:

*Number.*—Five.

*Shape.*—Generally ovoid, with acuminate tip and joined together at the lower parts.

*Character.*—The sepals are hooded over the bud before they divide and curl back when the flower opens.

*Color.*—Inside, 145-C and 146-A. Outside, 143-B/C and 144-C.

*Striae.*—Longitudinal.

Calyx:

*Shape.*—Bell-shaped.

*Size.*—Large.

*Aspect.*—Smooth.

Flower stem:

*Length.*—Averages about 80 cm., when cut at the tenth node.
*Character.*—Rigid and erect.
*Color.*—189-A/B.

THE FLOWER

Blooming habit: Recurrent, blooming profusely in the Spring, Midseason and Fall blooming periods with a tendency, however, to give few blooms in the Fall.
Size of flower: Large.
*Diameter.*—Averages about 8.7 cm.
*Depth.*—Averages about 6 cm.
Borne: Singly on a long, strong, upright stem.
Shape: When bloom first opens, high-centered. When bloom matures, dome-shaped.
Petalage:
*Number of petals.*—Averages about eighty-two.
*Arrangement.*—Imbricated.
*Form.*—Fan-shaped with heavily serrated outer end margins.
*Texture.*—Leathery.
*Appearance.*—Satiny.
*Color.*—Both inner and outer petals: Body — dark red, 46-B. Base — Greenish. Reverse side — 46-B/C.
Petaloids:
*Number.*—Less than ten.
*Size.*—Smaller than the petals.
*Color.*—The same as the petals.
Flower stem:
*Character.*—Upright with good strength.

*Color.*—189-A/B.
Discoloration after full bloom: A little.
Persistence: The flower petals hang on and dry.
Fragrance: Perceptible.
Lasting quality: As a cut flower, at least ten days in vase keeping.

REPRODUCTIVE ORGANS

Stamens:
*Number.*—Varies from six to seventeen.
*Arrangement.*—Encircling the ovary.
*Anthers.*—Size: Less than 4 mm. Color: Reddish.
*Filaments.*—Color: Reddish.
Pistils:
*Number.*—Three or four.
*Styles.*—Length: About 1.5 cm. Color: Reddish.
*Stigma.*—Color: Reddish.
Character of ovaries: Ribbed.

This carnation variety most nearly resembles the variety Scania (unpatented). Our new variety, however, differs from Scania by having a more serrated flower petal.

We claim:

1. A new and distinct standard variety of carnation plant substantially as herein shown and described, particularly characterized by its high productivity of medium sized brilliant dark ruby red flowers borne singly on rigid, upright stems having a recurrent blooming habit.

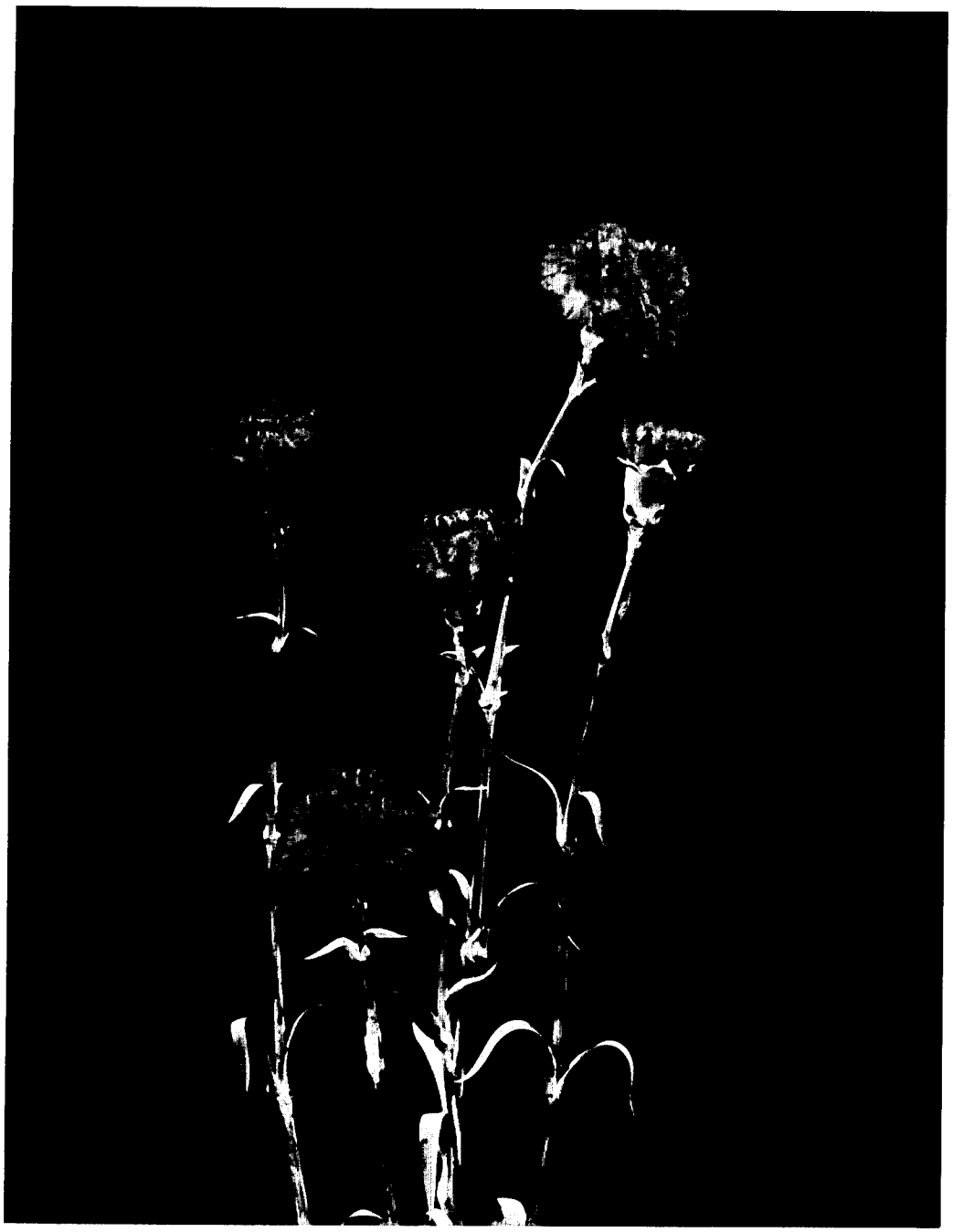

* * * * *